(12) United States Patent
Berlat

(10) Patent No.: US 8,021,683 B2
(45) Date of Patent: Sep. 20, 2011

(54) WOUND DRESSING

(75) Inventor: Alvin Berlat, Silverdale, WA (US)

(73) Assignee: Advanced Bio-Technologies, Inc., Suwanee, GA (US)

( * ) Notice: Subject to any disclaimer, the term of this patent is extended or adjusted under 35 U.S.C. 154(b) by 1138 days.

(21) Appl. No.: 10/479,877

(22) PCT Filed: Jul. 16, 2003

(86) PCT No.: PCT/GB03/03085

§ 371 (c)(1),
(2), (4) Date: May 3, 2004

(87) PCT Pub. No.: WO2004/006972

PCT Pub. Date: Jan. 22, 2004

(65) Prior Publication Data

US 2004/0175414 A1     Sep. 9, 2004

(30) Foreign Application Priority Data

Jul. 16, 2002 (GB) .................................. 0216427.5

(51) Int. Cl.
*A01N 25/00* (2006.01)
*A61K 9/70* (2006.01)

(52) U.S. Cl. .......................... 424/443; 424/405; 514/944

(58) Field of Classification Search .................. None
See application file for complete search history.

(56) References Cited

U.S. PATENT DOCUMENTS

| | | | |
|---|---|---|---|
| 5,292,530 A | 3/1994 | McCrea et al. | |
| 5,389,092 A | 2/1995 | Guillemet et al. | |
| 5,556,699 A | 9/1996 | Niira et al. | |
| 5,741,509 A | 4/1998 | Kushner | |
| 5,833,998 A * | 11/1998 | Biedermann et al. | 424/401 |
| 5,972,320 A * | 10/1999 | Moloney et al. | 424/65 |
| 6,155,265 A | 12/2000 | Hammerslag | |
| 6,183,766 B1 * | 2/2001 | Sine et al. | 424/405 |
| 6,827,929 B1 | 12/2004 | Lord et al. | |
| 2006/0110415 A1 | 5/2006 | Gupta | |
| 2008/0292560 A1 | 11/2008 | Tamarkin et al. | |
| 2008/0299220 A1 | 12/2008 | Tamarkin et al. | |
| 2009/0143333 A1 | 6/2009 | Palefsky et al. | |

FOREIGN PATENT DOCUMENTS

| | | |
|---|---|---|
| JP | 04-009327 | 1/1992 |
| JP | 09-194350 | 7/1997 |
| WO | WO-97/03710 | 2/1997 |
| WO | WO 00/47183 | 8/2000 |

OTHER PUBLICATIONS

Merck Index ($9^{th}$ Ed.) Entry No. 9812: Zinc Oxide.*
Dow Corning MSDS for silicone blend 225 (i.e. DC-225).*
Thixin R/ Thixcin R—properties bulletin; Elementis Specialties, Inc.*
U.S. Patent Documents—None.*
Thixin R/Thixcin R—properties bulletin; Elementis Specialties, Inc.; made available online Aug. 5, 2009.*
Merck Index (9th Ed.) Entry No. 9812: Zinc Oxide (1976).*
Dow Corning MSDS for silicone blend 225 (i.e. DC-225); Rev. Published Mar. 26, 2007.*

* cited by examiner

*Primary Examiner* — Robert A Wax
*Assistant Examiner* — Jeffrey T Palenik
(74) *Attorney, Agent, or Firm* — Shumaker, Loop & Kendrick, LLP

(57) ABSTRACT

A composition comprising a non-volatile silicone fluid in admixture with fumed silica, a volatile diluent and a silicone elastomer.

36 Claims, No Drawings

WOUND DRESSING

The present invention relates to silicone based compositions, a method of manufacturing such compositions and the use of such compositions in medicine. In particular, although not exclusively, the present invention provides a silicone based wound dressing.

Damage to the skin produced by injury or surgery for example cuts, wounds, and/or skin lesions may result in the production of scars rather than regeneration of the original tissue. Suitably, such scars are undesirable as they may not only create embarrassing cosmetic problems but the scar tissue also typically lacks the functionality of normal skin. For example, the sense of touch may be diminished or completely lost and weak spots may form where the scar tissue joins uninjured tissue. Various procedures and treatments have been developed with a view to decreasing the formation of scars and ameliorating existing scars.

Suitably, wound dressings comprising water bearing plastic films or hydrogels have been developed in an attempt to reduce scar formation and prevent the growth of pathogens at the wounded target tissue site. A particular disadvantage with hydrogel dressings is that they may not conform well to the changing topography of the body and thus they may exert different pressures on different parts of the body. Suitably, such hydrogel dressings may not completely cover the target tissue site. Moreover, as the water content of such hydrogel dressings may vary with atmospheric humidity, thus altering the effectiveness and lifetime of the dressing, a covering or top-coat is typically applied over the dressing. Still further, as the hydrogel dressing may be heavy, awkward and very difficult to maintain in the correct position, professional attention by doctors or nurses is usually required for proper maintenance.

Suitably, alternative wound dressings comprising silicone oils, also known as siloxanes, have been developed. Although silicone oils may exhibit good compatibility with human tissue and display desirable biological properties, for example allowing skin activity to function normally by permitting the passage of water vapour, gases and toxins from the skin whilst acting as a barrier to potential pathogens, typically silicone oils per se are in the form of free-flowing fluids/oils and do not exhibit the desired physical consistency to render them suitable for use as a wound dressing. Typically, the consistency of a stiff cream or grease is desirable for a wound dressing so that the dressing adheres sufficiently strongly to the underlying target tissue site and a deliberate effort is required to remove it from the target site.

In an attempt to increase the viscosity of silicone oils, wound dressings comprising a blend of a silicone oil and up to approximately 3% by weight fumed silica have been developed. Although such blends may provide improved consistency over the unblended silicone oils, typically more viscous blends are desirable to improve adhesion to the wound and to prevent the dressing from smearing (i.e. smear-proofing). However, silicone oil/fumed silica blends which exhibit a high viscosity and provide improved adhesion and "smear-proofing" are typically difficult to apply to the target tissue site without causing further injury and/or pain.

In an attempt to overcome the compromise of improved adhesion to the target tissue site versus inflicting further injury and/or pain, wound dressings comprising silicone oil, fumed silica and a volatile diluent have been developed. Suitably, the inclusion of a biocompatible volatile diluent may allow the wound dressing to be prepared in the form of a spreadable cream, gel or oil which can be applied to a wound without producing further injury or discomfort. After the blend is in place on the wound, evaporation of the volatile diluent from the composition typically produces a resultant composition having an increased viscosity which exhibits increased adhesion to the wound and increased smear-proofing. Although these compositions have gone some way in addressing the problems of producing a silicone oil based wound dressing having the desired consistency, a particular problem with such wound dressings is associated with the time required to elapse after the composition is applied to the target tissue site before the resultant composition exhibits the desired increased viscosity, adhesive and smear-proofing properties. Typically, the required evaporation time may be in the region of 15 minutes or longer before the composition exhibits sufficient adhesion to the target tissue site. Consequently, it may be necessary to immobilise the target site, or immobilise the composition on the target site, during this period in order to prevent the composition from falling off from the target tissue site whilst it attains the desired viscosity. Suitably, this may result in a decrease in the effectiveness and applicability of the composition, as it may be difficult to apply the composition to certain areas of the body, particularly those areas which are not readily immobilised and those areas which are not readily accessible. Moreover, the requirement of waiting for a fairly long period of time until the composition has attained the desired viscosity after it has been applied and the need to immobilise the target tissue site may result in decreased patient compliance and may necessitate professional application and attention by doctors or nurses.

The present invention therefore seeks to provide improved, compositions suitable for application to a target tissue site, in particular a target tissue site that is susceptible to pathogenic infection and/or scarring, especially to a skin lesion or wound.

According to a first aspect, the present invention provides a composition comprising a non-volatile silicone fluid in admixture with fumed silica, a volatile diluent and a silicone elastomer. Such a composition is referred to hereinafter as the composition of the present invention.

Suitably, the composition of the present invention seeks to solve the aforementioned technical problems associated with the application of a wound dressing to a target tissue site. Unexpectedly, it has been found that the inclusion of a silicone elastomer in the composition of the present invention may not only produce a composition having substantially the same viscosity as a comparable composition not including the silicone elastomer but also may promote evaporation of the volatile diluent from the composition of the present invention. Suitably, the composition of the present invention after application to a target tissue site may attain the desired increased viscosity, adhesive and anti-smearing properties due to evaporation of the volatile diluent in a shorter period of time compared with a substantially identical composition not including the silicone elastomer. Conveniently, it is typically unnecessary to immobilise the target tissue site or immobilise the composition on the target tissue site whilst the volatile diluent evaporates to form a resultant composition having the desired viscosity, adhesive and smear-proofing properties so that it may function as a wound dressing. Suitably, the effectiveness and applicability of, the composition of the present invention may be improved compared with a comparable composition not including the silicone elastomer, as the composition of the present invention may be applied to target tissue on bodily areas which are not readily accessible or not readily immobilised. Moreover, the composition of the present invention may be in the form of a spreadable cream, gel or oil which may be applied to a target tissue site without producing further injury or discomfort. Conveniently, the composition of the present invention may result in increased patient compliance and may negate the need for professional application and attention by doctors or nurses.

In essence, the composition of the present invention could be referred to as a "faster drying composition" compared to a substantially identical composition not including the silicone elastomer. Although only theory, it is believed that the silicone elastomer may promote evaporation of the volatile diluent from the composition of the present invention.

By the term "silicone elastomer" we mean a silicone polymer which, at room temperature, is capable of recovering substantially in shape and size after removal of a stretching force provided the elastic limit is not exceeded. Suitably, the silicone elastomer is a thixotropic solid so that the viscosity of the silicone elastomer decreases with time when a shear force is applied thereto.

Suitably, the silicone elastomer has a weight average molecular weight of greater than or equal to 150,000, preferably greater than or equal to 200,000, more preferably greater than or equal to 250,000, even more preferably greater than or equal to 300,000.

Preferably, the silicone elastomer comprises a silicone polymer. More preferably, the silicone elastomer is a silicone cross-polymer (i.e. a cross-linked silicone polymer). Even more preferably, the silicone elastomer comprises a dimethicone cross-polymer (i.e. a cross-linked dimethicone polymer). The silicone elastomer, particularly dimethicone cross-polymer, may be unsubstituted or substituted, for example substituted with a polyether such as polyethylene glycol (PEG). Most preferably, the silicone elastomer, particularly the dimethicone cross-polymer, is unsubstituted.

Suitably, when the silicone elastomer comprises a silicone cross-polymer, the silicone cross-polymer preferably comprises less than or equal to 10 wt % cross-linker, more preferably less than or equal to 8 wt % cross-linker, even more preferably less than or equal to 5 wt % cross-linker. Preferably, the silicone cross-polymer comprises greater than or equal to 1 wt % cross-linker, more preferably greater than or equal to 2 wt % cross-linker.

Preferably, the composition of the present invention comprises greater than or equal to 0.1% by weight, preferably greater than or equal to 0.2% by weight, more preferably greater than or equal to 0.25% by weight, more preferably greater than or equal to 0.3% by weight, most preferably greater than or equal to 0.5% by weight of the silicone elastomer. Preferably, the composition of the present invention comprises less than or equal to 10% by weight, more preferably less than or equal to 5% by weight, even more preferably less than or equal to 2% by weight, even more preferably less than or equal to 1.5% by weight, most preferably less than or equal to 1% by weight of the silicone elastomer. An especially preferred composition of the present invention comprises between 0.2 to 1% by weight, particularly 0.2 to 0.8% by weight of the silicone elastomer.

Conveniently, for ease of handling the silicone elastomer may be mixed with one or more lower viscosity silicone fluids, such as non-volatile silicone fluids and/or volatile silicone fluids as described hereinafter, for example a linear dimethicone or a cyclomethicone. Suitably, employing a mixture of silicone elastomer and non-volatile silicone fluid allows the elastomer to be mixed more easily with the other components of the composition of the present invention, namely fumed silica, non-volatile silicone fluid and the volatile diluent.

Preferably, the silicone elastomer is mixed with one or more lower viscosity non-volatile silicone fluids, especially a non-volatile linear dimethicone. Alternatively, the silicone elastomer is mixed with one or more volatile silicone fluids, especially a cyclomethicone as defined hereinafter, particularly decamethylpentasiloxane or dodecamethylhexasiloxane.

It will be appreciated, that when a silicone elastomer and lower viscosity silicone fluid mixture is employed in the composition of the present invention, the lower viscosity silicone fluid of the silicone elastomer and lower viscosity silicone fluid mixture may be identical to the volatile diluent or non-volatile silicone fluid in the composition of the present invention. Alternatively, the lower viscosity silicone fluid of the silicone elastomer and lower viscosity silicone fluid mixture may be different than the volatile diluent and the non-volatile silicone fluid in the composition of the present invention.

Particularly preferred mixtures of silicone elastomer and lower viscosity silicone fluids comprise a mixture of dimethicone cross-polymer as defined herein and a non-volatile dimethicone or non-volatile cyclomethicone or pentasiloxane. Especially preferred silicone cross-polymers include a dimethicone cross-polymer as defined herein in cyclomethicone silicone fluid, for example Dow Corning 9040 Silicone Elastomer Blend obtainable from Dow Corning Inc., Midland, Mich., USA, and a dimethicone cross-polymer in dimethicone silicone fluid, for example Dow Corning 9041 Silicone Elastomer Blend also obtainable from Dow Corning Inc.

Suitably, the mixture of silicone elastomer and lower viscosity silicone fluid is also thixotropic. Suitably, the mixture of silicone elastomer and lower viscosity silicone fluid exhibits a high viscosity when measured at 25° C. The viscosity of the mixture of silicone elastomer/lower viscosity silicone fluid may be determined using a rotational viscometer such as a Brookfield Synchro-lectric viscometer or a Wells-Brookfield Core/Plate viscometer available from Brookfield Engineering Laboratories, Stoughton, Mass., USA, employing test methods ASTM D-1084 (for a cup/spindle viscometer) and ASTM D-4287. (for a cone/plate viscometer). Suitably, viscometers designed for the high viscosity region (HA and HB models) are employed.

Suitably, the kinematic viscosity of a mixture comprising 15% by volume of the silicone elastomer and 85% by volume of a linear polydimethylsiloxane having a kinematic viscosity of 5 centistokes (namely Dow Corning 200 fluid 5 cSt available from Dow Corning) at 25° C. is greater than or equal to 220,000 centistokes, more preferably greater than or equal to 240,000 centistokes, most preferably greater than or equal to 250,000 centistokes when measured by the above methods. Preferably, the kinematic viscosity of a mixture comprising 15% by volume of the silicone elastomer and 85% by volume of a linear polydimethylsiloxane having a kinematic viscosity of 5 centistokes (namely Dow Corning 200 fluid 5 cSt available from Dow Corning) at 25° C. is less than or equal to 800,000 centistokes, more preferably less than or equal to 700,000 centistokes, most preferably less than or equal to 600,000 centistokes when measured by the above methods.

Suitably, the silicone elastomer per se is non-volatile. Suitably, the mixture of silicone elastomer and lower viscosity silicone fluid is non-volatile. In other words the silicone elastomer per se and mixture of silicone elastomer and lower viscosity silicone fluid, respectively, does not exhibit an appreciable vapour pressure at ambient temperature. Preferably, the volatile content of the silicone elastomer per se and mixture of silicone elastomer and lower viscosity silicone fluid, respectively, at 150° C. is less than or equal to 0.6% by weight, more-preferably less than or equal to 0.4% by weight, most preferably less than or equal to 0.3% by weight based on the total weight of the silicone elastomer per se and mixture of silicone elastomer and lower viscosity silicone fluid, respectively.

Suitably, when the silicone elastomer is in the form of a mixture of the silicone elastomer and a lower viscosity silicone fluid the silicone elastomer is present in an amount of less than or equal to 40% by volume, preferably less than or equal to 30% by volume, more preferably less than or equal to 20% by volume of the mixture. Suitably, when the silicone elastomer is in the form of a mixture of the silicone elastomer and a lower viscosity silicone fluid the silicone elastomer is present in an amount of greater than or equal to 5% by volume, preferably greater than or equal to 10% by volume, more preferably greater than or equal to 15% by volume of the mixture. The balance of the aforementioned mixtures typically substantially comprises one or more of said lower viscosity silicone fluids.

It will be appreciated by those skilled in the art when the silicone elastomer is in the form of a silicone elastomer and lower viscosity silicone fluid mixture, then it is necessary to include the appropriate amount of such a mixture so that the overall content of the silicone elastomer in the composition of the present invention preferably falls within the preferred limits as defined hereinbefore. Suitably, such an amount may be determined by routine experimentation based on the known concentration of the silicone elastomer and lower viscosity silicone fluid mixture.

Preferably, when the silicone elastomer is in the form of a mixture comprising the silicone elastomer and lower viscosity silicone fluid as defined herein, such a mixture is present in an amount of greater than or equal to 1% by weight, more preferably greater than or equal to 1.5% by weight, most preferably greater than or equal to 2% by weight based on the total weight of the composition. Preferably, when the silicone elastomer is in the form of a mixture comprising the silicone elastomer and lower viscosity silicone fluid as defined herein, such a mixture is present in an amount of less than or equal to 10% by weight, more preferably less than or equal to 7% by weight, most preferably less than or equal to 5% by weight based on the total weight of the composition. An especially preferred composition comprises 3% by weight of a mixture of silicone elastomer and lower viscosity silicone fluid as defined herein based on the total weight of the composition.

By the term "volatile diluent" we mean a diluent that substantially evaporates at normal body temperature (i.e. up to and including 38° C.) and atmospheric pressure. Preferably, the volatile diluent substantially evaporates at room temperature (i.e. 25° C.) and atmospheric pressure.

Suitably, the volatile diluent exhibits appreciable vapour pressure at ambient temperature. Preferably, the volatile diluent exhibits a heat of vaporization at 25° C. of greater than or equal to 50 kJkg$^{-1}$, more preferably greater than or equal to 75 kJkg$^{-1}$, even more preferably greater than or equal to 100 kJkg$^{-1}$, most preferably greater than or equal to 125 kJkg$^{-1}$. Preferably, the volatile diluent exhibits a heat of vaporization at 25° C. of less than or equal to 275 kJkg$^{-1}$, more preferably less than or equal to 250 kJkg$^{-1}$, even more preferably less than or equal to 225 kJkg$^{-1}$, most preferably less than or equal to 200 kJkg$^{-1}$.

Suitably, the volatile diluent exhibits a low viscosity when measured at 25° C. The viscosity of the volatile diluent may be measured using a glass capillary viscometer such as a Ubbelohde available from Fisher Scientific Co., Pittsburgh, Pa., USA, employing test method ASTM D-445, IP71.

Preferably, the volatile diluent has a kinematic viscosity of greater than or equal to 0.5 mm$^2$ s$^{-1}$, more preferably greater than or equal to 2 mm$^2$ s$^{-1}$, particularly greater than or equal to 3 mm$^2$ s$^{-1}$ when measured in accordance with the above method. Preferably, the volatile diluent has a kinematic viscosity of less than or equal to 10 mm$^2$ s$^{-1}$, more preferably less than or equal to 9 mm$^2$ s$^{-1}$, particularly less than or equal to 8 mm$^2$ s$^{-1}$ at 25° C. when measured in accordance with the above method.

Preferably, the volatile diluent is a volatile silicone fluid (such as a liquid) as these are typically compatible with the non-volatile silicone fluid. Suitably, the volatile silicone fluid comprises a silicone polymer, particularly a cyclomethicone silicone polymer. Preferred volatile silicone fluids are selected from a polydimethylcyclosiloxane, such as cyclohexasiloxane, cyclopentasiloxane, dodecamethylcyclohexasiloxane, decamethylcyclopentasiloxane, octamethylcyclotetrasiloxane; a polymethyldisiloxane such as hexamethyldisiloxane; or a polymethyltrisiloxane such as octamethyltrisiloxane. Highly preferred volatile silicone fluids comprise the polydimethylcyclosiloxanes, in particular cyclopentasiloxane and cyclohexasiloxanes, especially dodecylmethylcyclohexasiloxane and decamethylcyclopentasiloxane.

Examples of suitable volatile silicone fluids are Dow-Corning 244 which comprises a cyclomethicone octamethylcyclotetrasiloxane, Dow-Corning 245 which comprises a cyclomethicone decamethylcyclopentasiloxane Dow Corning 246 which comprises a cyclomethicone dodecamethyl cyclohexasiloxane and Dow Corning 345 which comprises a cyclomethicone decamethylcyclopentasiloxane.

Preferably, the weight average molecular weight of the volatile diluent is greater than or equal to 150, more preferably greater than or equal to 250, most preferably greater than or equal to 300. Preferably, the weight average molecular weight of the volatile diluent is less than or equal to 1,000, more preferably less than or equal to 800, even more preferably less than or equal to 600, most preferably less than or equal to 500.

Mixtures of volatile silicone fluids may also be used to alter the rate of volatilization if desired. The volatile diluent may be added to the mixture of non-volatile silicone fluid, fumed silica and silicone elastomer in any proportion required to reduce the viscosity of the composition of the present invention to produce an easy to apply oil or light grease. At very high dilution, for example if 1 part by weight of a mixture of non-volatile silicone fluid, fumed silica and silicone elastomer is added to 1000 parts by weight of the volatile diluent, then the product can be applied as a mobile fluid with a suitable applicator, such as a roll-on applicator, or even as a spray from a spray bottle. At the other extreme, as little as 1 part by weight of the volatile diluent may be added to 99 parts by weight of the non-volatile silicone, fumed silica and silicone elastomer blend to produce a more viscous composition to assist in its application.

Suitably, the volatile diluent is present at greater than or equal to 1%, more preferably greater than or equal to 5%, even more preferably greater than or equal to 10%, even more preferably greater than or equal to 15%, even more preferably greater than or equal to 20%, most preferably greater than or equal to 25% by weight based on the total weight of the composition of the present invention. Suitably, the diluent is present at less than or equal to 99.9%, preferably less than or equal to 80%, preferably less than or equal to 70%, preferably less than or equal to 60%, most preferably less than or equal to 50%, by weight based on the total weight of the composition of the present invention.

It will be appreciated if the silicone elastomer is in the form of a mixture of the silicone elastomer and a volatile silicone fluid, then the total amount of volatile diluent in the composition of the present invention (i.e. volatile silicone fluid of the elastomer and volatile silicone fluid mixture plus the volatile diluent per se) preferably falls within the above preferred ranges.

Suitably, the volatile diluent may form the balance of the composition of the present invention.

By the term "non-volatile silicone fluid" we include a silicone fluid that does not substantially evaporate from the composition of the present invention at normal body temperature (i.e. up to and including 38° C.) and atmospheric pressure. Preferably, the non-volatile silicone fluid does not substantially evaporate from the composition at room temperature (i.e. up to and including 25° C.) and at atmospheric pressure.

Suitably, the non-volatile silicone fluid per se does not exhibit an appreciable vapour pressure at ambient temperature. Preferably, the volatile content of the non-volatile silicone fluid per se at 150° C. is less than or equal to 0.8% by weight, more preferably less than or equal to 0.6% by weight, even more preferably less than or equal to 0.4% by weight, most preferably less than or equal to 0.3% by weight based on the total weight of the non-volatile silicone fluid per se.

Suitably, the non-volatile silicone fluid component forms the base of the composition of the present invention and provides the chemical properties of the barrier between the injured target tissue and the environment. Suitably, the non-volatile silicone fluid is a silicone polymer.

Preferably, the non-volatile silicone fluid is a non-volatile silicone oil. Preferably, the non-volatile silicone fluid has a kinematic viscosity at 25° C. of greater than or equal to 500 centistokes, more preferably greater than or equal to 5,000 centistokes, most preferably greater than or equal to 10,000 centistokes when measured by ASTM D-445, IP71 using a glass capillary viscometer as described herein. Preferably, the silicone fluid has a kinematic viscosity at 25° C. of less than or equal to 200,000 centistokes, more preferably less than or equal to 100,000 centistokes, most preferably less than or equal to 50,000 centistokes. Suitably, viscosities up to 100,000 centistokes may be measured by ASTM D-445, IP71 using a glass capillary viscometer, and viscosities above 100,000 centistokes may be measured using rotational viscometers and test methods ASTM D-1084 and ASTM D-4281. Highly preferred non-volatile silicone fluids have a kinematic viscosity at 25° C. of about 30,000 centistokes when measured by ASTM D-445, IP71 using a glass capillary viscometer.

Preferably, the non-volatile silicone fluid comprises a silicone polymer, particularly a linear silicone polymer, especially a linear dimethicone polymer. Suitably, the linear silicone polymer essentially includes no crosslinks. Highly preferred non-volatile silicone fluids comprise a polydimethylsiloxane polymer, especially a linear polydimethylsiloxane polymer.

Preferably, the weight average molecular weight of the non-volatile silicone fluid is greater than or equal to 1,500, more preferably greater than or equal to 2,500, most preferably greater than or equal to 5,000. Preferably the weight average molecular weight of the non-volatile silicone fluid is less than or equal to 100,000, more preferably less than or equal to 50,000, even more preferably less than or equal to 25,000, even more preferably less than or equal to 20,000.

Conveniently, in the composition of the present invention the silicone elastomer and if employed, the silicone elastomer and lower viscosity silicone fluid mixture, has a higher viscosity than the non-volatile silicone fluid which in turn has a higher viscosity than the volatile diluent.

It will be appreciated that by increasing the viscosity of the non-volatile silicone fluid in the composition of the invention may produce a composition having increased durability and resistance to removal from the target tissue site, particularly following evaporation of the volatile diluent from the composition. Similarly, by lowering the viscosity of the non-volatile silicone fluid component may produce a composition which may be more easily applied to and removed from the target tissue. By using the full range of silicone oil viscosities, the composition of the present invention may be tailored to the unique needs of each case. Silicone fluids having viscosities of about 30,000 centistokes at 25° C. are especially preferred as they provide a balance of residual durability and ease of applicability. A particularly preferred non-volatile silicone fluid is Dow Corning 200 a linear polydimethyl siloxane polymer having a viscosity at 25° C. of about 30,000 centistokes produced by Dow-Corning Inc. (Midland, Mich.).

Preferably, the non-volatile silicone fluid is present in an amount of greater than or equal to 20% by weight, more preferably greater than or equal to 25% by weight, even more preferably greater than or equal to 30% by weight, most preferably greater than or equal to 35% by weight based on the total weight of the composition of the present invention. Preferably, the non-volatile silicone fluid is present in an amount of less than or equal to 65% by weight, more preferably less than or equal to 60% by weight, even more preferably less than or equal to 55% by weight based on the total weight of the composition of the present invention. An especially preferred composition of the present invention comprises 40 to 50% by weight non-volatile silicone fluid based on the total weight of the composition of the present invention.

It will be appreciated if the silicone elastomer is in the form of a mixture of the silicone elastomer and non-volatile silicone fluid, then the total amount of non-volatile silicone fluid in the composition of the present invention (i.e. non-volatile silicone of the silicone elastomer and non-volatile silicone fluid mixture plus the non-volatile silicone fluid per se) preferably falls within the above preferred ranges.

Suitably, the fumed silica provides a micro-skeletal structure when dispersed in the non-volatile silicone fluid to provide a gel. Preferably, the fumed silica is amorphous. The viscosity of the non-volatile silicone fluid may be dramatically increased when mixed (i.e. blended) with suitable quantities of fumed silica to form, for example a non-fluid grease-like gel. Any amorphous fumed silica that suitably thickens the non-volatile silicone fluid component may be used. Such fumed silicas include both untreated types and types that have been chemically treated to alter the fumed silica surface. Examples of suitable fumed silicas include but are not limited to Aerosil™ 90, 130, 200, 300, 380, R202, R805, R812, R972, R974 (Degussa Corporation, Ridgefield Park, N.J.) and CAB-O-SIL™ TS-720 and M-5 (Cabot Corporation, Tuscola, Ill.). Generally, Aerosil™ 200, Aerosil™ R974, CAB-O-SIL™ TS-720 and any other generally equivalent products from other manufacturers of fumed silicas are preferred as they suitably thicken non-volatile silicone fluids. Typically, the larger the quantity of fumed silica in the blend, the more viscous is the resultant gel.

Preferably, the fumed silica is present in an amount of greater than or equal to 0.25% by weight, more preferably greater than or equal to 0.5% by weight, even more preferably greater than or equal to 1% by weight, most preferably greater than or equal to 2% by weight based on the total weight of the composition of the present invention. Preferably, the fumed silica is present in an amount of less than or equal to 10% by weight, more preferably less than or equal to 8% by weight, even more preferably less than or equal to 6% by weight, most preferably less than or equal to 5% by weight based on the total weight of the composition of the present invention. A particularly preferred composition of the present invention comprises 2.5% to 3.5% by weight, particularly 3% by weight fumed silica based on the total weight of the composition of the present invention.

Preferably, in the composition of the present invention the blend of non-volatile silicone fluid and fumed silica comprises from greater than or equal to 0.25%, more preferably greater than or equal to 0.5%, most preferably greater than or equal to 1% by weight fumed silica. Preferably, in the composition of the present invention the blend of non-volatile silicone fluid and fumed silica comprises less than or equal to 12%, more preferably less than or equal to 9%, most preferably less than or equal to 5% by weight fumed silica. Such compositions typically provide a balance of thickness and workability.

Preferably, in the composition of the present invention the blend of non-volatile silicone fluid and fumed silica comprises from less than or equal to 99.75%, more preferably less than or equal to 99.5%, most preferably less than or equal to 99% by weight non-volatile silicone fluid. Preferably, in the composition of the present invention the blend of non-volatile silicone fluid and fumed silica comprises greater than or equal to 88%, more preferably greater than or equal to 91%, most preferably greater than or equal to 95% by weight non-volatile silicone fluid.

Preferably, in the composition of the present invention the blend of the non-volatile silicone fluid and fumed silica is present in an amount of greater than or equal to 1%, preferably greater than or equal to 22%, preferably greater than or equal to 24.9%, preferably greater than or equal to 47%, preferably greater than or equal to 49.9%, preferably greater than or equal to 57%, preferably greater than or equal to 59.9%, preferably greater than or equal to 62%, preferably greater than or equal to 64.9% by weight based on the total weight of the composition of the present invention. Preferably, in the composition of the present invention the blend of the non-volatile silicone fluid and fumed silica is present in an amount of less than or equal to 98.9%, preferably less than or equal to 96%, preferably less than or equal to 94.9%, preferably less than or equal to 92%, preferably less than or equal to 89.9%, preferably less than or equal to 87%, preferably less than or equal to 84.9%, preferably less than or equal to 82%, preferably less than or equal to 79.9%, preferably less than or equal to 77%, preferably less than or equal to 74.9%, preferably less than or equal to 72% by weight based on the total weight of the composition of the present invention.

Preferably, the composition of the present invention comprises 1 to 50 parts by weight of the silicone elastomer, 1 to 100 parts by weight fumed silica, 400 to 600 parts by weight volatile diluent and 400 to 600 parts by weight of non-volatile silicone fluid. More preferably, the composition of the present invention comprises 1 to 20 parts by weight of the silicone elastomer, 10 to 50 parts by weight fumed silica, 400 to 600 parts by weight volatile diluent and 400 to 600 parts by weight of non-volatile silicone fluid.

Suitably, the composition of the present invention has a lower viscosity than a comparable composition not including the volatile diluent i.e. a composition comprising a blend of a non-volatile silicone fluid, fumed silica and the silicone elastomer. Consequently, the composition of the present invention may be prepared in the form of a spreadable cream, gel, oil or light grease which can be applied to a wound without producing further injury of discomfort. Suitably, after the composition of the present invention is in place on the wound, evaporation of the volatile diluent therefrom, produces a resultant composition typically having an increased viscosity that is substantially equivalent to that of a blend of the non-volatile silicone fluid, silicone elastomer and fumed silica alone. In other words, a coating having a viscosity of a stiff cream, grease or film may be formed from a spreadable cream, thereby providing increased wound adhesion and smear proofing, without producing further damage to the wound or undue pain and discomfort during application.

It will be appreciated by those skilled in the art that the consistency of the composition of the present invention may be adjusted by varying the quantity of the volatile diluent, silicone elastomer, non-volatile silicone fluid and fumed silica. Consequently, the composition of the present invention may be in the form of films and sheets, as well as a spreadable cream, gel, oil or light grease. Typically, the physical and chemical properties of the residual non-volatile silicone fluid, silicone elastomer and fumed silica blend are unaltered after evaporation of the volatile diluent. However, it will be appreciated, particularly for highly viscous silicone fluid, silicone elastomer and fumed silica blends, that traces of the volatile diluent may remain in the composition after application which may eventually be driven off by body heat.

Preferably, the composition of the present invention is in the form of a gel or cream. Typically, this provides a balance of residual durability of the ultimate composition after evaporation of the volatile diluent and ease of applicability.

Preferably, the composition of the present invention (e.g. fumed silica, non-volatile silicone fluid, volatile diluent and silicone elastomer) has a kinematic viscosity of greater than or equal to 1,000 centistokes, preferably greater than or equal to 5,000 centistokes, more preferably greater than or equal to 10,000 centistokes when measured using a glass capillary viscometer using test method ASTM D-445, IP71 at 25° C. Preferably, the composition of the present invention has a kinematic viscosity of less than or equal to 25,000 centistokes, more preferably less than or equal to 22,000 centistokes, most preferably less than or equal to 20,000 centistokes at 25° C. when measured using a glass capillary viscometer using test method ASTM D-445, IP71.

Preferably, the resultant composition after evaporation of the volatile diluent from the composition of the present invention (i.e. after application) has a kinematic viscosity of greater than or equal to 27,000 centistokes, more preferably greater than or equal to 30,000 centistokes when measured at 25° C. using a glass capillary viscometer using test method ASTM D-445, IP71 at 25° C.

Preferably, the resultant composition of the present invention has a kinematic viscosity of less than or equal to 45,000 centistokes, more preferably less than or equal to 40,000 centistokes, most preferably less than or equal to 35,000 centistokes after evaporation of the volatile diluent when measured using a glass capillary viscometer using test method ASTM D-445, IP71 at 25° C.

Conveniently, the composition of the present invention (e.g. fumed silica, non-volatile silicone fluid, volatile diluent and silicone elastomer) having an initial specific viscosity within the aforementioned limits typically attains the resultant desired final viscosity (i.e. after evaporation of the volatile diluent therefrom) within the aforementioned limits faster than a comparable composition having the same initial specific viscosity not including the silicone elastomer.

Suitably, a composition of the present invention in the form of a gel/cream having an initial kinematic viscosity of 15,000 to 20,000 centistokes at 25° C. (ASTM D-445, IP71) produces a resultant composition having a kinematic viscosity of 30,000 to 35,000 centistokes at 25° C. (ASTM D-445, IP71) in less than or equal to 10 minutes, more preferably less than or equal to 8 minutes, even more preferably less than or equal to 6 minutes, even more preferably less than or equal to 4 minutes, most preferably less than or equal to 3 minutes following evaporation of the volatile diluent therefrom after application of the composition of the present invention to a target tissue site (i.e. when the composition is subjected to a temperature of approximately 38° C.).

A highly preferred composition of the present invention comprises:
1 to 5% by weight fumed silica as defined herein;
35 to 65% by weight non-volatile silicone fluid as defined herein;
25 to 65% by weight volatile diluent as defined herein; and
1 to 5% by weight of a mixture of silicone elastomer and lower viscosity silicone fluid as defined herein,
wherein the component parts of the composition total 100% by weight.

A further highly preferred composition of the present invention consists essentially of:
1 to 5% by weight fumed silica as defined herein;
35 to 65% by weight non-volatile silicone fluid as defined herein;
25 to 65% by weight volatile diluent as defined herein;
1 to 5% by weight of a mixture of silicone elastomer and lower viscosity silicone fluid as defined herein; and,
0 to 30% by weight of a pharmaceutical active agent as defined herein.

In accordance with a preferred embodiment of the present invention, the composition includes one or more pharmaceutical active agents.

By the term "pharmaceutical active agent" we include any compound, including pharmaceutical acceptable derivatives such as a salt, solvate and pro-drug and any composition which may be used for the curative and/or prophylactic treatment of a medical condition of a human or animal.

Preferably, the pharmaceutical active agent possesses antibacterial, anti-inflammatory, antiviral and/or antifungal activity. An essentially preferred pharmaceutical active agent comprises an antibacterial agent. An alternative especially preferred pharmaceutical active agent comprises an anti-inflammatory agent.

Preferably, the pharmaceutical active agent is present in an amount of less than or equal to 50%, more preferably less than or equal to 30%, more preferably less than or equal to 10%, most preferably less than or equal to 3% by weight based on the total weight of the composition of the present invention. Preferably, the pharmaceutical active agent is present in an amount of greater than or equal to 0.1%, more preferably greater than or equal to 0.5%, especially greater than or equal to 1.0% by weight based on the total weight of the composition of the present invention.

Suitably, the pharmaceutical active agent may be in the form of a liquid, gel or powder. Preferably, the pharmaceutical active agent is in the form of a powder, especially a powder that is insoluble in a typical pharmaceutical acceptable diluent, such as water or alcohol.

Preferred antibacterial agents include antibiotic zeolites, chlorohexidine, polymyxin B sulphate, benzachromium chloride, benzamycin, clindamycin, erythromycin, tetracycline, mupirocin, bacitracin zinc and neomycin sulphate. Especially preferred antibacterial agents include antibiotic zeolites.

Preferred antibiotic zeolites include those in which the ion-exchangeable ions of the zeolite such as sodium ions, potassium ions, calcium ions, magnesium ions and iron ions have been partially or completely ion-exchanged with antibiotic ions. Examples of suitable antibiotic ions include silver, copper, zinc, mercury, tin, lead, bismuth, cadmium, chromium and thallium ions. Preferred antibiotic metal ions are silver, copper and zinc ions. These ions may be used alone or in combination. A particularly preferred antibiotic ion is silver.

Either natural or synthetic zeolites may be used as the "zeolite component". Examples of such zeolites are disclosed in U.S. Pat. No. 5,556,699 which is incorporated herein by reference. Methods for preparing the antibiotic zeolites for use in the composition of the present invention may be prepared by techniques well known to those skilled in the art, for example, as disclosed in U.S. Pat. No. 5,556,699.

Preferably, the antibiotic metal ions are present in the zeolite in an amount of greater than or equal to 0.1%, preferably greater than or equal to 0.25%, more preferably greater than or equal to 0.75%, most preferably greater than or equal to 1% by weight of the zeolite. Preferably, the antibiotic metal ions in the zeolite are present in an amount of less than or equal to 15%, more preferably less than or equal to 10%, most preferably less than or equal to 5% by weight of the zeolite. By the term % by weight of the zeolite we mean expressed in terms of the weight of the zeolite weighed after drying at a temperature 110° C.

It will be appreciated by those skilled in the art that although antibiotic zeolites possess suitable antibiotic activity they typically require complex formulations in order to make them suitable for topical application to a target tissue. Surprisingly, it has been found that an antibiotic zeolite may be incorporated into the composition of the present invention without the need for further complicated processing techniques. Moreover, the resultant composition of the present invention comprising the antibiotic zeolite may exhibit enhanced antibacterial activity compared with the antibiotic zeolite alone.

Preferred anti-inflammatory agents include non-steroidal anti-inflammatory drugs (NSAIDs). Preferred NSAIDs include phenyl propionic acids such as ibuprofen, naproxen, ketoprofen and flurbiprofen. Another preferred NSAID is acetyl salicylic acid. Highly preferred NSAIDs include ibuprofen and acetyl salicylic acid, particularly acetyl salicylic acid.

Suitably, the composition of the present invention may include one or more pharmaceutically acceptable adjuvants. In particular, the composition of the present invention may include an antioxidant. When an antioxidant is present, the antioxidant is present in an amount of less than or equal to 15%, more preferably less than or equal to 10% by weight based on the total weight of the composition of the present invention. Preferably the antioxidant is present in an amount of greater than or equal to 1% by weight, more preferably greater than or equal to 3% by weight based on the total weight of the composition of the present invention.

Preferred antioxidants include alpha-tocopherol, gamma-tocopherol, delta-tocopherol, extracts of natural origin which are rich in tocopherol, L-ascorbic acid and its sodium or calcium salts, palmityl-DL-ascorbic acid, propyl gallate, octyl gallate, dodecyl gallate, butylhydroxyanisole (BHA) gallate and butylhydroxytoluene (BHT) gallate. A highly preferred antioxidant is alpha-tocopherol (Vitamin E).

According to a further aspect, the present invention provides a method for delivering a pharmaceutical active agent as defined hereinbefore to a target tissue by administering a composition of the present invention including a pharmaceutical active agent to the target tissue.

Suitably, the composition of the present invention as defined herein is suitable for use in medicine, particularly for reducing and/or preventing scarring by administering the composition to a wound, cut and/or skin lesion. Conveniently, the composition of the present invention may be administered topically to the target tissue site.

Conveniently, the composition of the present invention may ameliorate or reduce existing scars when applied thereto.

According to yet a further aspect, the present invention provides a method for reducing and/or preventing scarring, particularly hypertrophic or keloid scars, comprising administering a composition of the present invention as defined herein to a wound, cut or skin lesion. Similarly, the present invention provides a wound dressing comprising a composition of the present invention as defined herein. Suitably, the wound dressing may be in a form as described herein e.g. gel, stiff cream, film etc.

According to a further aspect, the present invention provides a method of manufacturing a composition of the present invention as defined herein comprising contacting, preferably mixing, a non-volatile silicone fluid with fumed silica, a volatile diluent and a silicone elastomer (and a pharmaceutical active agent, if present). Preferably, the volatile diluent and silicone elastomer (and pharmaceutical active agent, if present) is added to a blend of the non-volatile silicone fluid and fumed silica.

Preferably, the compositions of the present invention are prepared by methods well known to those skilled in the art for example by using stirrers, blenders, mills and the like and other methods suitable for blending silicone oils and fumed silica. In addition, pressure vessels and condensing systems may be used to retain the volatile diluent in the composition of the present invention. Suitably, the non-volatile silicone fluid and fumed silica blend is initially prepared and then admixed with the volatile diluent and silicone elastomer. Alternatively, the blend of the non-volatile silicone fluid and fumed silica and volatile diluent may be formed in one stage and the silicone elastomer added thereto. It will be appreciated by those skilled in the art that the pharmaceutical active agent, when present may be added at any stage of the preparation of the composition of the present invention.

Typically, when the composition of the present invention includes a pharmaceutical active agent or pharmaceutically acceptable adjuvant a masterbatch comprising the pharmaceutical active agent or adjuvant, the mixture of a blend of non-volatile silicone fluid, fumed silica, the silicone elastomer, and volatile diluent, is initially prepared. Suitably, the masterbatch includes the pharmaceutical active agent and/or adjuvant at 20% by weight of the masterbatch. The masterbatch may then be diluted with a mixture of non-volatile silicone fluid, fumed silica, volatile diluent and silicone elastomer to form a composition of the present invention having the desired concentration of the pharmaceutical active agent and/or adjuvant as described herein (typically 1 to 5 wt % of the composition for an antibiotic zeolite). Advantageously, such a processing technique may ensure correct dispersion of the pharmaceutically active agent in the composition of the present invention, whilst minimizing the agglomerization of the pharmaceutically active agent, thereby resulting in an increased activity of the pharmaceutically active agent in the composition of the present invention.

Alternatively, or additionally, a dispersant such as magnesium stearate, may be added to the masterbatch to promote dispersion of the pharmaceutically active agent within the composition of the present invention. Typically, an anhydrous dispersant is mixed with the anhydrous pharmaceutically active agent before compounding. Preferably, 10% by weight of the dispersant is included. The pharmaceutically active agent/dispersant mixture may then be used to form a masterbatch as described hereinbefore. Preferably, particularly in the case of an antibiotic zeolite, the compositions of the present invention are prepared under anhydrous conditions as the inclusion of water in the compositions of the present invention may promote discoloration and agglomerization of the pharmaceutical active agent, thereby resulting in decreased efficiency of the composition.

It will be appreciated by those skilled in the art, that the compositions of the present invention may be administered by non-medical professional staff. Suitably, the compositions of the present invention are applied to the target tissue by means well known to those skilled in the art, such as application with a spatula, a roll-on or spray type applicator.

According to a further aspect, the present invention provides a method for treating a wound comprising applying a composition of the present invention to a wound.

According to a further aspect, the present invention provides a topical pharmaceutical delivery system comprising a composition of the present invention and a pharmaceutical active agent.

According to a further aspect, the present invention provides a wound dressing comprising a composition of the present invention. It will be appreciated that the wound dressing may be considered as a self-drying wound dressing, as after it is applied to a target tissue site bodily heat only is required to effect evaporation of the volatile diluent.

According to a further aspect, the present invention provides the use of a silicone elastomer for preparing a wound dressing. Particularly, a self-drying wound dressing following application to a bodily target tissue site.

The invention will now be described by way of the following non-limiting examples.

The following raw materials were employed:
Dow Corning 200 having a viscosity at 25° C. of about 30,000 centistokes (non-volatile silicone fluid);
Fumed silica—Aerosil 200;
Dow Corning 245 comprising decamethylpentasiloxane having a viscosity of 4 $mm^2$ $s^{-1}$ at 25° C. (volatile diluent);
Dow Corning 246 comprising dodecamethyl cyclohexasiloxane having a viscosity of 7.7 $mm^2$ $s^{-1}$ at 25° C. (volatile diluent);
Dow Corning 9040 Silicone Elastomer Blend comprising dimethicone cross-polymer in cyclomethicone and having a viscosity of 250,000 to 580,000 centistokes at 25° C.;
Dow Corning 9041 Silicone Elastomer Blend comprising dimethicone cross-polymer in dimethicone silicone fluid and having a viscosity of 300,000 to 500,000 centistoke at 25° C.;
Agion™ an antibiotic zeolite, in which the ion-exchangeable ions of the zeolite have been partially or fully exchanged with silver ions, supplied by Agion Technologies of 60 Audubon Road, Wakefield, Mass. 01880, USA.

EXAMPLE 1

Preparation of a Composition of the Present Invention

A blend comprising 45% by weight Dow Corning 245, 50% by weight Dow Corning 200, 3% by weight fumed silica (Aerosil 200) and 2% by weight Dow Corning 9040 Silicone Elastomer Blend was stirred at ambient temperature using a JH Day Pony Mixer, under anhydrous conditions, for 2 hours. The resultant product comprised a gel having a viscosity of 19,000 to 21,000 centistokes at 25° C. when measured by a glass capillary viscometer by test method ASTM D-445, IP71.

EXAMPLE 2

Preparation of a Comparative Composition

A blend comprising 45% by weight Dow Corning 245, 52% by weight Dow Corning 200 and 3% by weight fumed silica (Aerosil 200) was stirred at ambient temperature using a JH Day Pony Mixer, under anhydrous conditions, for 2 hours. The resultant product comprised a gel having a viscosity of 18,000 to 20,000 centistokes at 25° C. when measured by a glass viscometer by test method ASTM D-445, IP71.

EXAMPLE 3

Drying Time of Example 1 versus Example 2

Ten separate human subjects were selected. The composition of Example 1 was added in sufficient quantity to cover a 2 inch area and the composition of Example 2 was applied to a similar sized area to respective forearms of each subject. Each subject was asked to monitor the perceived stiffening and adherence of each of the compositions to the skin and note the time (referred to as end time) when no further increase in stiffening and adherence was perceived (e.g. effective time when substantially all the volatile diluent had evaporated from the compositions). The results for each composition for ten subjects were averaged (Mean End Time) and are presented below in Table 1.

TABLE 1

|  | Mean End Time |
|---|---|
| Example 1 | 4.4 minutes |
| Example 2 | 15.2 minutes |

The results demonstrate that the composition of Example 1 including a silicone elastomer dries much faster than a comparable composition not including the silicone elastomer (Example 2) when both compositions are applied to a bodily target tissue site.

EXAMPLE 4

Preparation of a Composition of the Present Invention Plus an Antibacterial Agent A masterbatch comprising 20 weight percent Agion™ and the balance of the masterbatch (80 wt %) comprising a mixture of Aerosil 200, Dow Corning 200, Dow Corning 245 and Dow Corning 9040 silicone elastomer (3% by weight Aerosil 200:50% by weight Dow Corning 200:45% by weight Dow Corning 245;2% by weight Dow Corning 9040) was prepared by adding the Agion powder to a blend of the non-volatile silicone fluid, fumed silica, volatile silicone diluent and silicone elastomer. The masterbatch was stirred with a JH Day Pony Mixer at ambient temperature, under anhydrous conditions, for up to 2 hours to effect dispersion of the Agion™ powder. The masterbatch was then diluted with the desired amount of the mixture of Aerosil 200, Dow Corning 200, Dow Corning 245 and Dow Corning 9040 (3% by weight 50% by weight 45% by weight: 2% by weight (Aerosil: Dow Corning 200: Dow Corning 245: Dow Corning 9040)) to form the following compositions of the present invention in the form of a gel having a viscosity of 19,000 to 21,000 centistokes at 25° C. when measured by a glass capillary viscometer by test method ASTM D-445, IP71.

|  | Agion™ % by wt of the composition | Aerosil:Dow Corning 200:Dow Corning 245:Dow Corning 9040 (3:50:45:2) % by weight of the composition |
|---|---|---|
| Example 4a | 1 | 99 |
| Example 4b | 2 | 98 |
| Example 4c | 5 | 95 |

EXAMPLE 5

In-vivo Wound Healing/Antibacterial Activity

Three human volunteers having wounds which had started to develop into keloid scars were selected.

The composition of Example 4a (2 g) was spread over the scar of the first volunteer so that the composition adhered to the tissue site.

A control composition (2 g) comprising a mixture of 3% by weight Aerosil 200, 50% by weight Dow Corning 200, 45% by weight Dow Corning 245 and 2% by weight Dow Corning 9040 was spread over the scar of the second volunteer so that the resulting composition adhered to the tissue site.

Agion™ powder alone (40 mg) was placed over the scar of the third volunteer and the powder immobilised on the tissue site with a transparent adhesive plaster.

Each of the patients were monitored over a 1 month period and the reduction in redness (representing a decrease in infection) and flattening of the scar (representing scar amelioration and/or prevention and/or reduction) was recorded. The results are presented in Table 2 below.

TABLE 2

| Sample | Reduction in Redness | Flattening of Scars |
|---|---|---|
| Example 4a | Immediate reduction in redness after 1 to 2 days, further decrease in redness occurred. | Steady reduction in level of scar. After one month scar showing visible signs of disappearing. |
| Control | Minor decrease in redness after 1 month. | Reduction in level of scar after 1 month but not as significant as Example 4a as scar present after 1 month and no signs of scar disappearing. |
| Agion™ alone | Reduction in redness observed after 4 days. | A scar developed. |

The results demonstrate that the composition of the present invention including an antibacterial agent not only reduces the redness of the scar (indicative of antibacterial activity) but also prevents and/or ameliorates scarring. Moreover, there appears to be a synergistic effect of antibacterial and/or scar reducing effects employing a combination of the antibiotic zeolite and the composition of the present invention.

EXAMPLE 6

The following compositions as listed in Table 3 were prepared in accordance with Example 4 above except the Agion antibiotic zeolite was replaced with the appropriate pharmaceutical active agent.

TABLE 3

| | Pharmaceutical Active Agent (% by weight of the composition) | Aerosil:Dow Corning 200: Dow Corning 245:Dow Corning 9040 (3:50:45:2) (% by the weight of the composition) |
|---|---|---|
| Example 6a | Chlorohexidine acetate (2% by wt) | 98% by wt |
| Example 6b | Benzamycin (3% by wt) | 97% by wt |
| Example 6c | Erythromycin (3% by wt) | 97% by wt |
| Example 6d | Acetylsalicylic acid (5% by wt) | 95% by wt |
| Example 6e | Vitamin E (4% by wt) | 96% by wt |
| Example 6f | Ibuprofen (20% by wt) | 80% by wt |

EXAMPLE 7

The following compositions as listed in Table 4 were prepared in accordance with Example 1 as detailed above.

TABLE 4

| | Aerosil % by wt | Dow Corning 245 % by wt | Dow Corning 246 % by wt | Dow Corning 200 % by wt | Dow Corning 9040 % by wt | Dow Corning 9041 % by wt |
|---|---|---|---|---|---|---|
| Example 7a | 1 | 50 | — | 45 | 4 | — |
| Example 7b | 4 | 40 | — | 50 | 1 | — |
| Example 7c | 6 | 45 | — | 45 | 4 | — |
| Example 7d | 6 | — | 45 | 45 | 4 | — |
| Example 7e | 3 | 48 | — | 45 | — | 4 |

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A wound dressing including a composition consisting of a non-volatile silicone fluid in admixture with fumed silica, a volatile diluent and a silicone elastomer.

2. A wound dressing as claimed in claim 1 wherein the silicone elastomer comprises a silicone cross-polymer.

3. A wound dressing as claimed in claim 2 wherein the silicone cross-polymer comprises a dimethicone cross-polymer.

4. A wound dressing as claimed in claim 1 wherein the silicone elastomer is in the form of a mixture comprising the silicone elastomer in a lower viscosity silicone fluid.

5. A wound dressing as claimed in claim 4 wherein the lower viscosity silicone fluid comprises a linear dimethicone or cyclomethicone.

6. A wound dressing as claimed in claim 4 wherein the mixture of silicone elastomer and lower viscosity silicone fluid has a viscosity of greater than of equal to 220,000 centistokes when measured at 25° C.

7. A wound dressing as claimed in claim 4 wherein the mixture of silicone elastomer and lower viscosity silicone fluid has a viscosity of less than or equal to 800,000 centistrokes when measured at 25° C.

8. A wound dressing as claimed in claim 4 wherein the mixture of silicone elastomer and lower viscosity silicone fluid is present in an amount of greater than or equal to 1% by weight of the composition.

9. A wound dressing as claimed in claim 4 wherein the mixture of silicone elastomer and lower viscosity silicone fluid is present in an amount of less than or equal to 10% by weight of the composition.

10. A wound dressing as claimed in claim 1 wherein the composition is a mixture comprising 15% by volume of the silicone elastomer and 85% by volume of a linear polydimethylsiloxane having a viscosity of 5 centistokes at 25° C. has a kinematic viscosity of greater than or equal to 220,000 centistokes when measured according to ASTM D-1084.

11. A wound dressing as claimed in claim 1 wherein the composition is a mixture comprising 15% by volume of the silicone elastomer and 85% by volume of a linear polydimethylsiloxane having a viscosity of 5 centistokes at 25° has a kinematic viscosity of greater than or equal to 800,000 centistokes when measured according to ASTM D-1084.

12. A wound dressing as claimed in claim 1 wherein the firmed silica is present in an amount of greater than or equal to 1% by weight of the composition.

13. A wound dressing as claimed in claim 1 wherein the volatile diluent is present in an amount of greater than or equal to 25% by weight of the composition.

14. A wound dressing as claimed in claim 1 wherein volatile diluent comprises a volatile silicone fluid.

15. A wound dressing as claimed in claim 14 wherein the volatile silicone fluid comprises a silicone polymer.

16. A wound dressing as claimed in claim 1 wherein the non-volatile silicone fluid has a kinematic viscosity of less than or equal to 200,000 centistokes when measured at 25° C.

17. A wound dressing as claimed in claim 1 wherein the non-volatile silicone fluid comprises a silicone polymer.

18. A wound dressing as claimed in claim 1 wherein the non-volatile silicone fluid is present in an amount of greater than or equal to 20% by weight of the composition.

19. A wound dressing as claimed in claim 1 wherein the composition consists of:
   1 to 5% by weight fumed silica; 35 to 65% by weight non-volatile silicone fluid;
   25 to 65% by weight volatile diluent; and
   1 to 5% by weight of a mixture of silicone elastomer and lower viscosity silicone fluid,
   wherein the component parts of the composition total 100% by weight.

20. A wound dressing as claimed in claim 1 wherein the composition is in the form of a spreadable cream, gel, light grease or mobile spray on fluid.

21. A wound dressing including a composition consisting of a non-volatile silicone fluid in admixture with fumed silica, a volatile diluent, a silicone elastomer, and a pharmaceutical active agent.

22. A wound dressing as claimed in claim 21 wherein the pharmaceutical active agent is selected from antibiotic zeolites, chlorohexidine, polymyxin B sulphate, benzachromium, clindamycin, erythromycin, tetracycline, mupirocin, bacitracin zinc, neomycin sulphate, ibuprofen, naproxen, ketoprofen, flurbiprofen, acetyl salicylic acid or a combination thereof.

23. A wound dressing as claimed in claim 21 wherein the pharmaceutical active agent is selected from an antibacterial agent or from a non-steroidal anti-inflammatory drug.

24. A method of manufacturing a wound dressing as defined in claim 1 comprising contacting a non-volatile silicone fluid with fumed silica, a volatile diluent and a silicone elastomer.

25. A method for reducing scarring comprising administering a wound dressing as defined in claim 1 to a target tissue site.

26. A method for treating a wound comprising applying a wound dressing as defined in claim 21 to a wound.

27. A wound dressing as claimed in claim 1, wherein the composition is self-drying.

28. A wound dressing as claimed in claim 15 wherein the silicone polymer comprises a cyclomethicone.

29. A wound dressing as claimed in claim 17 wherein the silicone polymer comprises a linear dimethicone.

30. A wound dressing as claimed in claim 21 further wherein the pharmaceutical active agent has antibacterial anti-inflammatory activity, antiviral activity, antifungal activity, or a combination thereof.

31. A wound dressing as claimed in claim 23 wherein the antibacterial agent comprises an antibiotic zeolite.

32. A wound dressing as claimed in claim 23 wherein the non-steroidal anti-inflammatory drug comprises acetyl salicylic acid.

33. A wound dressing including a composition consisting of a non-volatile silicone fluid in admixture with fumed silica, a volatile diluent, a silicone elastomer, and an antioxidant.

34. A method for preparing a wound dressing comprising providing a wound dressing including a composition consisting of a non-volatile silicone fluid in admixture with fumed silica, a volatile diluent and a silicone elastomer.

35. A method for preparing a wound dressing comprising providing a wound dressing including a composition consisting of a non-volatile silicone fluid in admixture with fumed silica, a volatile diluent, a silicone elastomer, and a pharmaceutical active agent.

36. A method for preparing a wound dressing comprising providing a wound dressing including a composition consisting of a non-volatile silicone fluid in admixture with fumed silica, a volatile diluent, a silicone elastomer, and an antioxidant.

* * * * *